US011875880B2

(12) United States Patent
Shilov (10) Patent No.: US 11,875,880 B2
(45) Date of Patent: *Jan. 16, 2024

(54) SYSTEMS AND METHODS FOR CALCULATING PROTEIN CONFIDENCE VALUES (71) Applicant: DH Technologies Development PTE. LTD., Singapore (SG)

(72) Inventor: Ignat V. Shilov, Palo Alto, CA (US)

(73) Assignee: DH Technologies Development Pte Ltd., Singapore (SG)

(*) Notice: Subject to any disclaimer, the term of this patent is extended or adjusted under 35 U.S.C. 154(b) by 983 days.

This patent is subject to a terminal disclaimer.

(21) Appl. No.: 16/679,155

(22) Filed: Nov. 9, 2019

(65) Prior Publication Data

US 2020/0075132 A1 Mar. 5, 2020

Related U.S. Application Data (62) Division of application No. 13/697,707, filed as application No. PCT/US2011/036193 on May 12, 2011, now Pat. No. 10,497,466.

(60) Provisional application No. 61/334,763, filed on May 14, 2010.

(51) Int. Cl.
*G16C 20/20* (2019.01)
*G16B 40/10* (2019.01)
*G16B 20/00* (2019.01)
*G16B 15/00* (2019.01)

(52) U.S. Cl.
CPC ............. *G16C 20/20* (2019.02); *G16B 15/00* (2019.02); *G16B 20/00* (2019.02); *G16B 40/10* (2019.02)

(58) Field of Classification Search
CPC ................................ G16C 20/20; G16B 40/10
See application file for complete search history.

(56) References Cited

U.S. PATENT DOCUMENTS

2006/0030053 A1* 2/2006 Seymour ............... C07K 14/79
702/19

OTHER PUBLICATIONS

Nesvizhskii et al. Anal. Chem. 2003, 75, 4646-4658.*

* cited by examiner

*Primary Examiner* — Lori A. Clow
*Assistant Examiner* — Emilie A Neulen
(74) *Attorney, Agent, or Firm* — Kasha Law LLC; John R. Kasha; Kelly L. Kasha (57) ABSTRACT

A method is disclosed for calculating and recalculating protein confidence values by recalculating peptide confidence values in proteomic analysis. A plurality of scans are performed of a sample that is proteolytically digested into surrogate peptide analytes. A plurality of spectra are obtained, and a plurality of peptides are identified. A protein database is searched for proteins matching peptides from the plurality of peptides. Peptide confidence values are determined for the set of peptides. A protein confidence value is calculated for each protein in the set of proteins. A protein from the set of proteins with a largest protein confidence value is selected, the largest protein confidence value for the protein is saved, the protein from the set of proteins is removed, and peptides corresponding to the protein is removed from the set of peptides. The protein confidence value is recalculated for each protein in the set of proteins.

6 Claims, 8 Drawing Sheets

SYSTEMS AND METHODS FOR CALCULATING PROTEIN CONFIDENCE VALUES

CROSS-REFERENCE TO RELATED APPLICATION

This application is a divisional application of U.S. patent application Ser. No. 13/697,707 filed Nov. 13, 2012, filed as Application No. PCT/US11/36193 on May 12, 2011, which claims the benefit of U.S. Provisional Patent Application No. 61/334,763 filed May 14, 2010, the disclosures of which are incorporated by reference herein in their entireties.

INTRODUCTION

Confidence values play an important role in proteomic analysis. In proteomics analysis, a sample is proteolytically digested into surrogate peptide analytes that are identified by tandem mass spectrometry coupled with a database search. The identifications of these surrogate peptide analytes are then used to infer the detection of their parent proteins. Peptide confidence values are assigned to surrogate peptide analytes based on a heuristic or a database search, for example. Protein confidence values for the parent proteins are calculated from the peptide confidence values. The protein confidence values for the parent proteins are then used to distinguish parent proteins actually found in the sample from random or false positive results.

BRIEF DESCRIPTION OF THE DRAWINGS

The skilled artisan will understand that the drawings, described below, are for illustration purposes only. The drawings are not intended to limit the scope of the present teachings in any way.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

Figure 1:
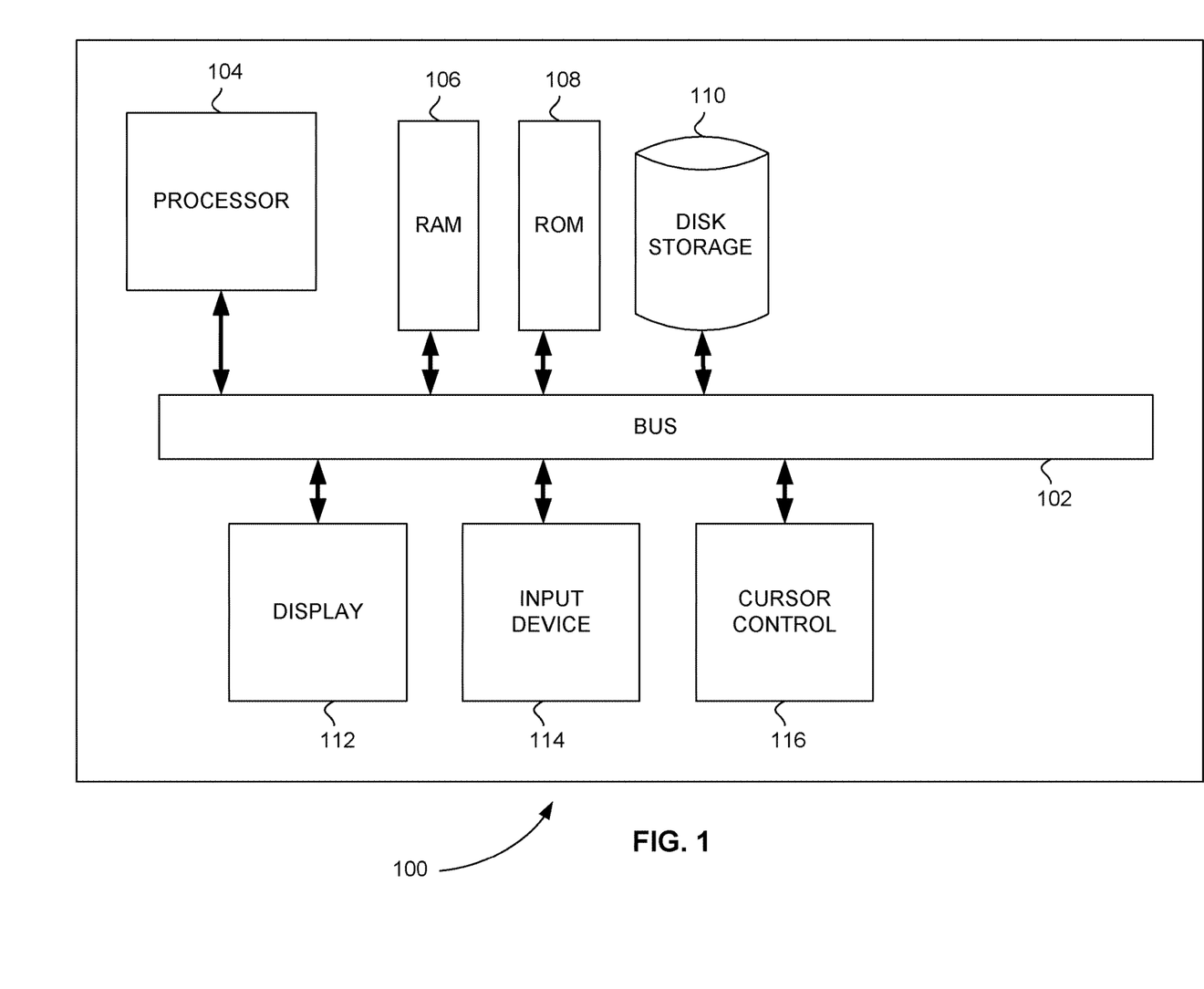
FIG. 1 is a block diagram that illustrates a computer system, upon which embodiments of the present teachings may be implemented.

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for determining base calls, and instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Methods of Data Processing

As described above, protein confidence values calculated during proteomic analysis of a sample can be used to distinguish proteins actually found in the sample from random or false positive results. Each protein confidence value of an identified protein is calculated from one or more confidence values of the one or more peptides that were used to identify the protein. The assignment of peptide confidence values can be based on a heuristic or a database search, for example.

Figure 2:
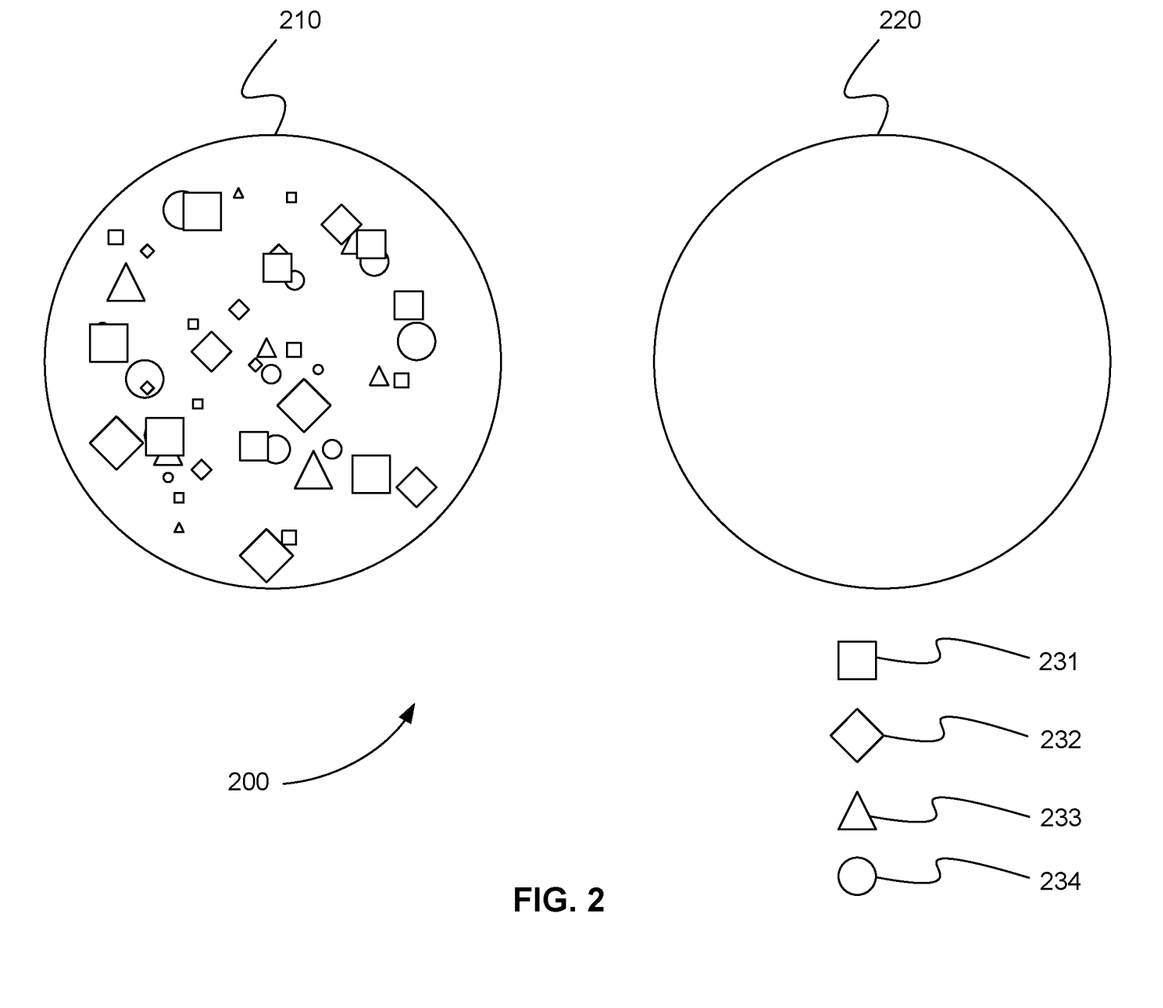
FIG. 2 is a diagram of a set of unassigned peptides and a set of assigned peptides before any peptides are assigned, in accordance with various embodiments.

FIG. 2 is a diagram 200 of a set of unassigned peptides 210 and a set of assigned peptides 220 before any peptides are assigned, in accordance with various embodiments. Set of unassigned peptides 210 includes a first group of peptides 231, a second group of peptides 232, a third group of peptides 233, and a fourth group of peptides 234. First group of peptides 231, second group of peptides 232, and third group of peptides 233 represent multiple peptides that correspond to a single protein. Fourth group of peptides 234 represents a group of singleton peptides, or multiple peptides that each correspond to a different protein. Note that the relative size of the label of each peptide in each group corresponds to its initial relative peptide confidence value. Set of assigned peptides 220 is empty in diagram 200, showing that no peptides are yet assigned.

Once one or more peptides are assigned to a protein, they are removed from set of unassigned peptides 210 and added to set of assigned peptides 220. One or more peptides are assigned to a protein by calculating a protein confidence value for each protein identified using one or more peptide confidence values of the one or more corresponding peptides, ranking the identified proteins by protein confidence value, and assigning the corresponding one or more peptides to the protein with the highest confidence value. Calculating a protein confidence value for each protein identified using one or more peptide confidence values of the one or more corresponding peptides includes, for example, increasing the protein confidence value as the number of peptides identifying the same protein increases. In other words, if a first protein is identified from a first peptide and a second peptide, a second protein is identified from a third peptide, and the first peptide, the second peptide, and the third peptide all have the same peptide confidence value, then the first protein is given a higher confidence value. As a result, groups of larger numbers of peptides identifying a protein are generally assigned first.

As described above, set of unassigned peptides 210 of diagram 200 includes groups 231, 232, and 233 that represent multiple peptides that each correspond to the same single protein and group 234 that represents the group of singleton peptides. In set of unassigned peptides 210, group 234 appears as a small percentage of the total number of unassigned peptides.

Figure 3:
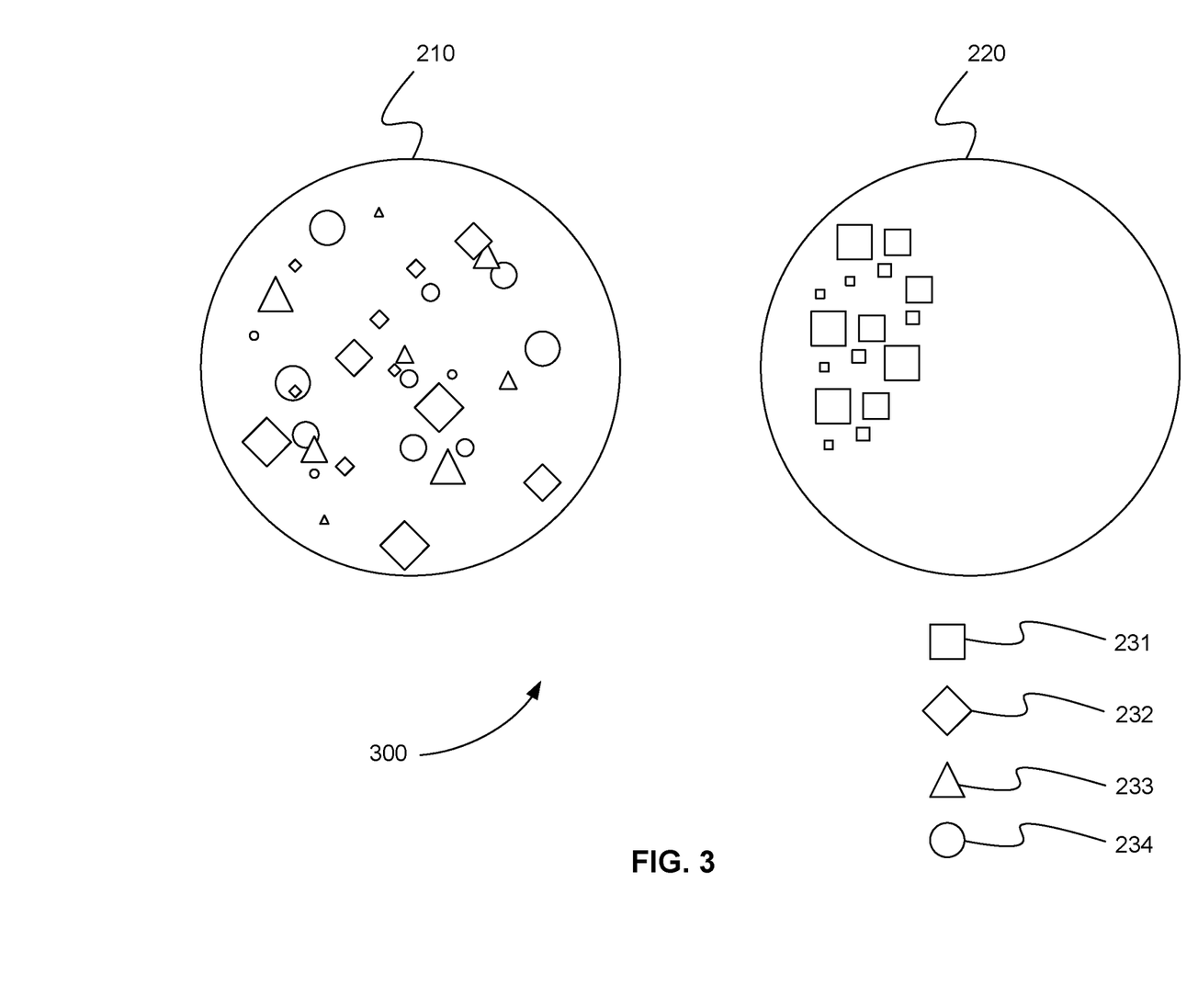
FIG. 3 is a diagram of a set of unassigned peptides and a set of assigned peptides after a first group of peptides is assigned, in accordance with various embodiments.

FIG. 3 is a diagram 300 of a set of unassigned peptides 210 and a set of assigned peptides 220 after a first group of peptides 231 is assigned, in accordance with various embodiments. First group of peptides 231 includes the largest number of peptides identifying a protein, for example. First group of peptides 231 is effectively moved from set of unassigned peptides 210 to set of assigned peptides 220. Set of unassigned peptides 210 now has a fewer number of unassigned peptides and fourth group of peptides 234, representing the group of singleton peptides, is now a larger percentage, but still not a significant percentage of the total number of unassigned peptides.

Figure 4:
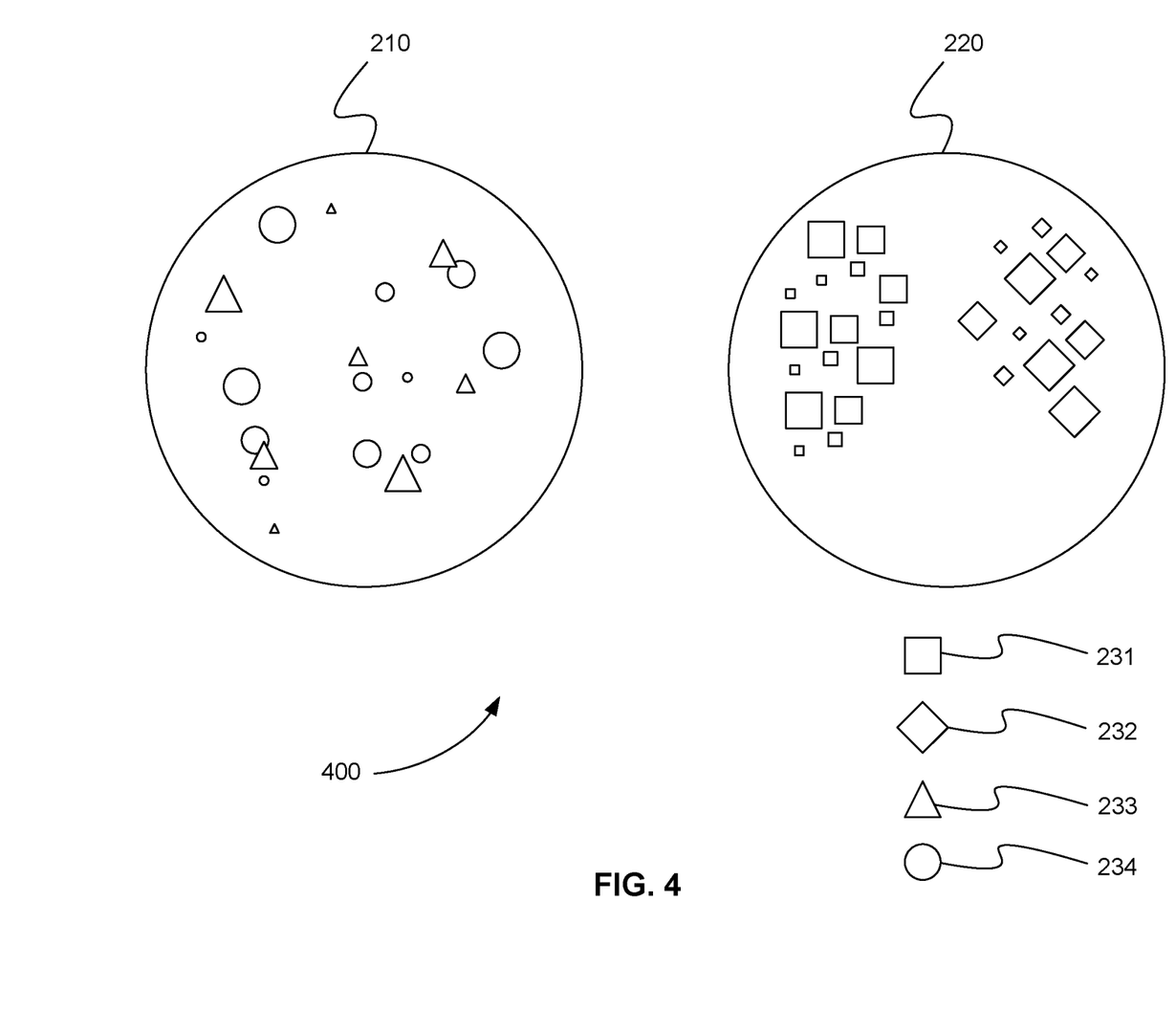
FIG. 4 is a diagram of a set of unassigned peptides and a set of assigned peptides after a second group of peptides is assigned, in accordance with various embodiments.

FIG. 4 is a diagram 400 of a set of unassigned peptides 210 and a set of assigned peptides 220 after a second group 232 of peptides is assigned, in accordance with various embodiments. Second group of peptides 232 is effectively moved from set of unassigned peptides 210 to set of assigned peptides 220. Set of unassigned peptides 210 now has a fewer number of unassigned peptides and fourth group of peptides 234, representing the group of singleton peptides, is now an even larger and significant percentage of the total number of unassigned peptides.

Figure 5:
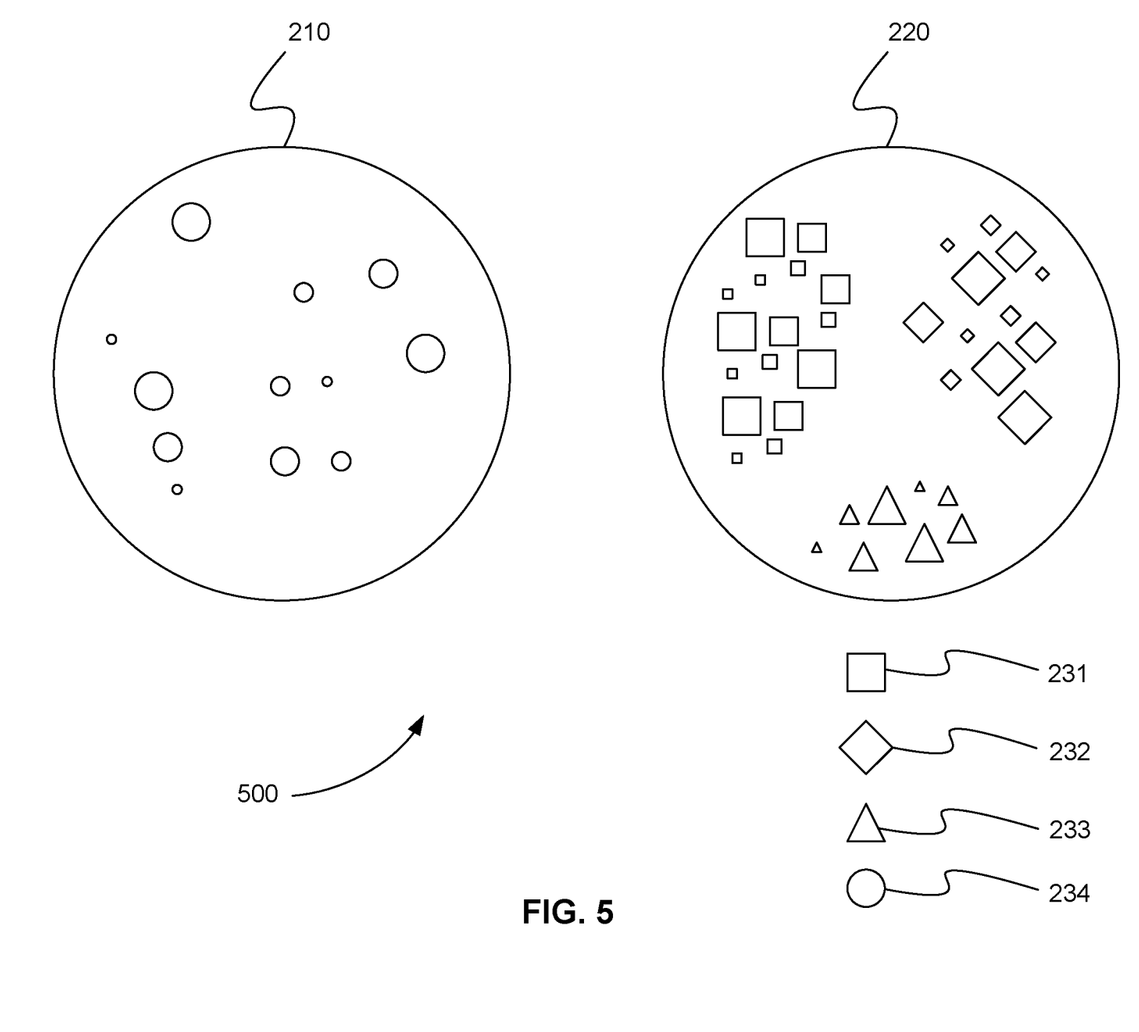
FIG. 5 is a diagram of a set of unassigned peptides and a set of assigned peptides after a third group of peptides is assigned, in accordance with various embodiments.

FIG. 5 is a diagram 500 of a set of unassigned peptides 210 and a set of assigned peptides 220 after a third group 233 of peptides is assigned, in accordance with various embodiments. Third group of peptides 233 is effectively moved from set of unassigned peptides 210 to set of assigned peptides 220. Set of unassigned peptides 210 now only includes fourth group of peptides 234, representing the group of singleton peptides.

FIGS. 2-4 show that as peptides are assigned to proteins, the potential influence of fourth group of peptides 234 on protein confidence values increases. FIG. 5 shows that the final peptides assigned to proteins are based directly on the peptide confidence values of fourth group of peptides 234.

Because protein confidence values are calculated from peptide confidence values and peptide confidence values do not change as peptides are assigned to proteins, the protein confidence values are dependent on the initial confidence values of the peptides. These initial peptide confidence values are based on a model for the relationship between the amount of evidence in data for a peptide and the probability of correctness of a peptide. These values do not include any information about the sample or about relationships across peptides. As a result, the protein confidence values may be inaccurate if peptides with comparable evidence do not actually have comparable probability of correctness once information about the sample is taken into account. Practically this may result in the calculation of high (false positive) protein confidences values, especially for singleton peptides, and the assignment of some singleton peptides before the assignment of multiple peptides corresponding to the same protein.

In various embodiments, after each assignment of one or more peptides to a protein, the peptide confidence values of unassigned peptides that are used to calculate protein confidence values are updated based on the effect of the removal of the one or more peptides assigned to the protein. In other words, information about the sample is used to recalculate the confidence values of unassigned peptides. This information about the sample can be, for example, hidden correlations between peptides.

Figure 6:
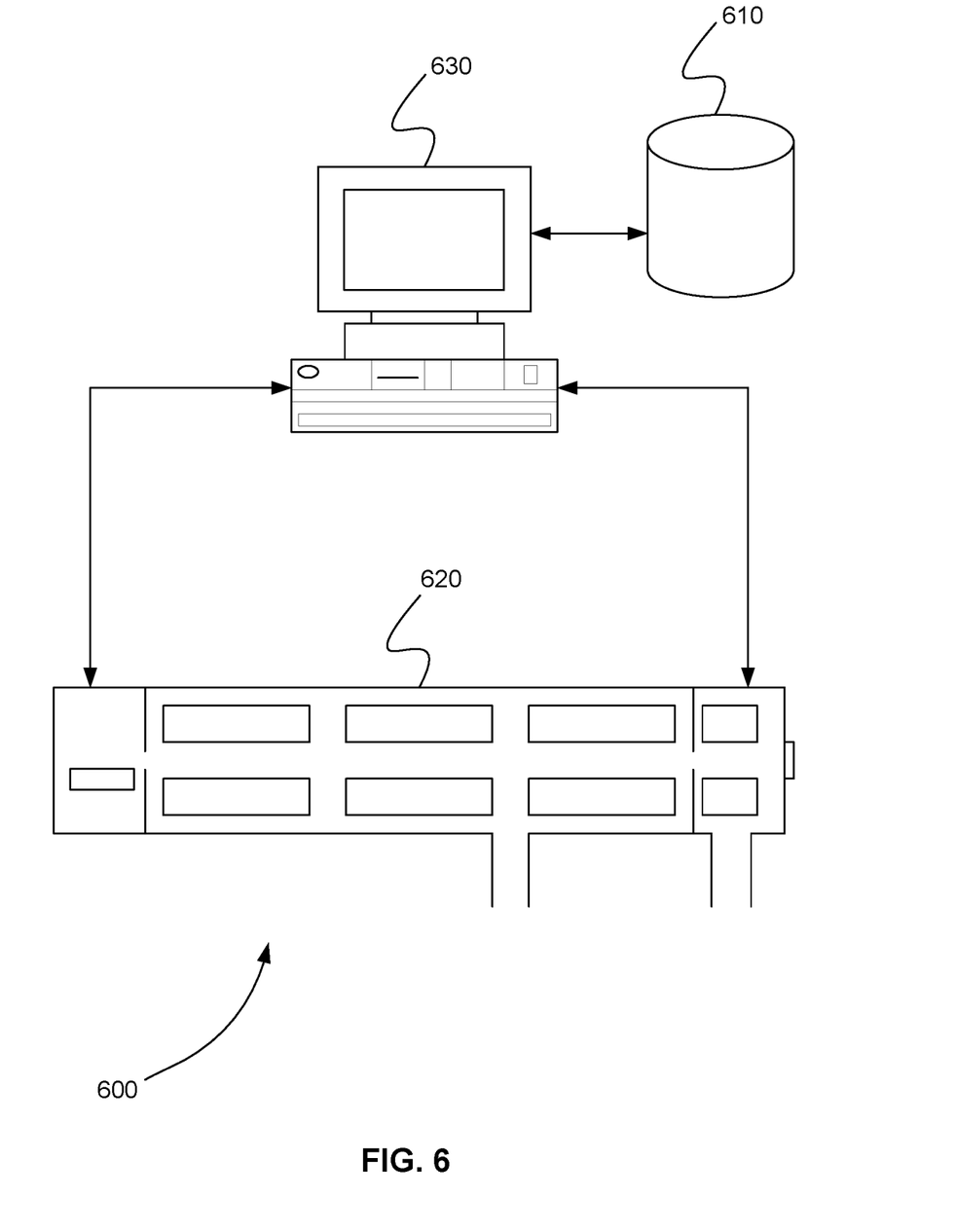
FIG. 6 is a schematic diagram showing a system for calculating protein confidence values in proteomic analysis, in accordance with various embodiments.

FIG. 6 is a schematic diagram showing a system 600 for calculating protein confidence values in proteomic analysis, in accordance with various embodiments. System 600 includes protein database 610, mass spectrometer 620, and processor 630. Protein database 610 can include a storage device connected directly to processor 630 or a storage device accessed by processor 630 through another processor (not shown). Protein database 610 stores a plurality of known protein sequences that can be searched.

Mass spectrometer 620 can include, but is not limited to including, a time-of-flight (TOF), quadrupole, ion trap, Fourier transform, Orbitrap, or magnetic sector mass spectrometer. Mass spectrometer 620 can also include a separation device (not shown). The separation device can perform a separation technique that includes, but is not limited to, liquid chromatography, gas chromatography, capillary electrophoresis, or ion mobility.

A sample is proteolytically digested into peptides. Mass spectrometer 620 is used to perform a plurality of scans of the sample producing a plurality of spectra. In various embodiments, more than one mass spectrometer can be used to perform a plurality of scans of the sample producing a plurality of spectra.

Processor 630 is processor in communication with protein database 610 and mass spectrometer 620. This communication can include data and control information. Processor 630 performs a number of steps.

Processor 630 obtains the plurality of spectra from mass spectrometer 630. Processor 630 identifies a plurality of peptides from the plurality of spectra. The plurality or peptides are identified using peak lists, for example. Processor 630 searches protein database 610 for proteins matching one or more peptides from the plurality of peptides producing a set of matched or targeted proteins and a corresponding set of identifying peptides. Processor 630 determines a peptide confidence value for each peptide in the set of identifying peptides. Processor 630 calculates a protein confidence value for each protein in the set of targeted proteins. The protein confidence value is based on one or more peptide confidence values of one or more corresponding peptides from the set of identifying peptides. Processor 630 selects the protein from the set of targeted proteins with the largest protein confidence value, saves the protein confidence value for the protein, removes the protein from the set of targeted proteins, and removes one or more peptides corresponding to the protein from the set of identifying peptides. Finally, processor 630 recalculates the protein confidence value for each protein in the set of targeted proteins based on one or more peptide confidence values of one or more corresponding peptides from the set of identifying peptides and an effect of removing the one or more peptides corresponding to the removed protein from the set of identifying peptides.

In various embodiments, processor 630 repeats the steps of selecting the protein with the largest protein confidence value, saving the protein confidence value for the protein, removing the protein from the set of targeted proteins, removing the one or more peptides corresponding to the protein from the set of identifying peptides, and recalculating the protein confidence value for each protein remaining in the set of targeted proteins iteratively until all proteins are removed from the set of targeted proteins.

In various embodiments, processor 630 determines the initial peptide confidence values for the set of identifying peptides using a target-decoy method or a heuristic. In an exemplary target-decoy method, processor 630 creates protein-like decoy sequences and searches these decoy sequences along with the sequences of a target protein database to determine confidence values. Protein database 610 is used as the target protein database, for example. Matches with decoy sequences correspond to random matches, for example.

In various embodiments, the peptide confidence values for the set of identifying peptides and the protein confidence value for each protein in the set of targeted proteins are Bayesian probabilities.

In various embodiments, processor 630 calculates a protein confidence value for each protein in the set of proteins from one or more peptide confidence values of one or more corresponding peptides from the set of peptides under the assumption that the observation of each peptide is an independent event. For example, if $C_i$ is the peptide confidence of the $i^{th}$ peptide of one or more peptides corresponding to a protein, the protein confidence value, $P_p$, can be calculated from the following equation.

$$P_p = 1 - \Pi(1 - C_i) \qquad \text{Equation 1}$$

In various embodiments, processor 630 recalculates the protein confidence value for each protein in the set of targeted proteins from one or more peptide posterior confidence values of one or more corresponding peptides from the set of identifying peptides. For example, Equation 1 is also used to recalculate the protein confidence value, $P_p$, of each protein in the set of targeted proteins after a protein has been removed. However, instead of directly using the peptide confidence of the $i^{th}$ peptide, $C_i$, of one or more peptides corresponding to the protein, the posterior peptide probability of the $i^{th}$ peptide, $P(+|B)$, is used.

In various embodiments, processor 630 calculates the one or more peptide posterior confidence values of one or more corresponding peptides from the set of peptides from the one or more peptide confidence values and a prior peptide confidence value. For example, the posterior peptide probability of the $i^{th}$ peptide, $P(+|B)$, is calculated using the following equation, for example, where $P(B|+)$ is the peptide confidence of the $i^{th}$ peptide, $C_i$, $P(+)$ is the prior probability of selecting a true positive, and $P(B)$ is the marginal probability of observing the peptide with given confidence.

$$P(+|B) = \frac{P(B|+) \cdot P(+)}{P(B)} \qquad \text{Equation 2}$$

In various embodiments, processor 630 calculates the prior peptide confidence value from a sum of all peptide confidence values of peptides currently in the set of identifying peptides and a sum of all confidence values of peptides currently in the set of peptides and all confidence values of peptides removed from the set of identifying peptides. For example, the prior peptide confidence value, P(+), is calculated from the following equation where M is the number of peptides currently in the set of identifying peptides and N is the sum of the number of peptides currently in the set of identifying peptides and the number of peptides that were removed from the set of identifying peptides.

$$P(+) = \frac{\sum_{i=1}^{M} C_i \cdot C_i}{\sum_{i=1}^{M} C_i \cdot C_i + \sum_{i=1}^{N} C_i \cdot (1 - C_i)} \qquad \text{Equation 3}$$

Figure 7:
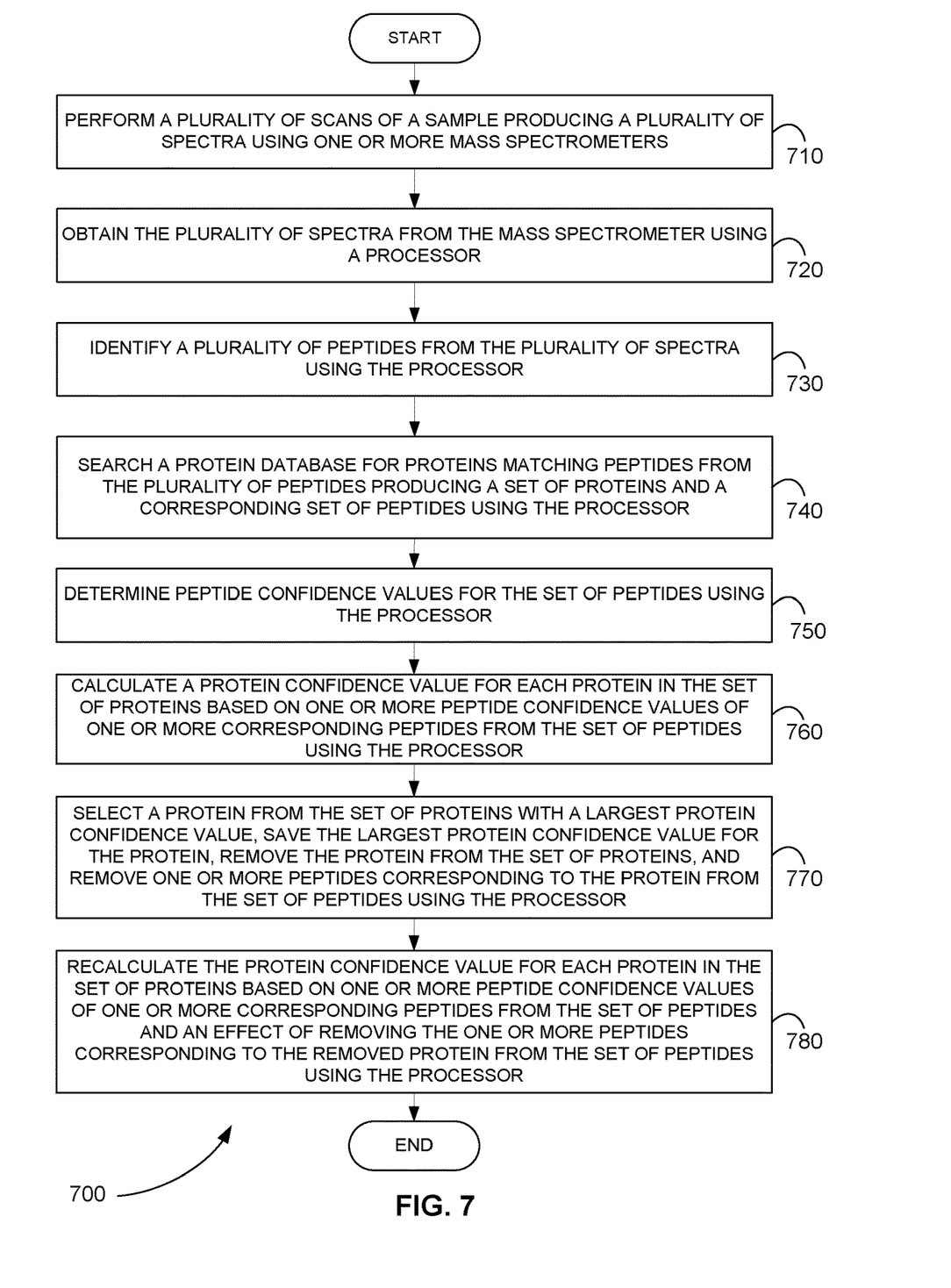
FIG. 7 is an exemplary flowchart showing a method for calculating protein confidence values in proteomic analysis, in accordance with various embodiments.

FIG. 7 is an exemplary flowchart showing a method 700 for calculating protein confidence values in proteomic analysis, in accordance with various embodiments.

In step 710 of method 700, a plurality of scans of a sample is performed producing a plurality of spectra using one or more mass spectrometers.

In step 720, the plurality of spectra is obtained from the one or more mass spectrometers using a processor.

In step 730, a plurality of peptides is identified from the plurality of spectra using the processor.

In step 740, a protein database is searched for proteins matching peptides from the plurality of peptides producing a set of proteins and a corresponding set of peptides using the processor.

In step 750, peptide confidence values for the set of peptides are determined using the processor.

In step 760, a protein confidence value is calculated for each protein in the set of proteins based on one or more peptide confidence values of one or more corresponding peptides from the set of peptides using the processor.

In step 770, a protein is selected from the set of proteins with a largest protein confidence value, the largest protein confidence value is saved for the protein, the protein is removed from the set of proteins, and one or more peptides corresponding to the protein are removed from the set of peptides using the processor.

In step 780, the protein confidence value is recalculated for each protein in the set of proteins based on one or more peptide confidence values of one or more corresponding peptides from the set of peptides and an effect of removing the one or more peptides corresponding to the removed protein from the set of peptides using the processor.

In various embodiments, steps 770 and 780 can be repeated until all proteins are removed from the set of proteins or until the best possible protein confidence is below a threshold of interest, for example.

In various embodiments, a computer program product includes a tangible computer-readable storage medium whose contents include a program with instructions being executed on a processor so as to perform a method for calculating protein confidence values in proteomic analysis. This method is performed by a system of distinct software modules.

Figure 8:
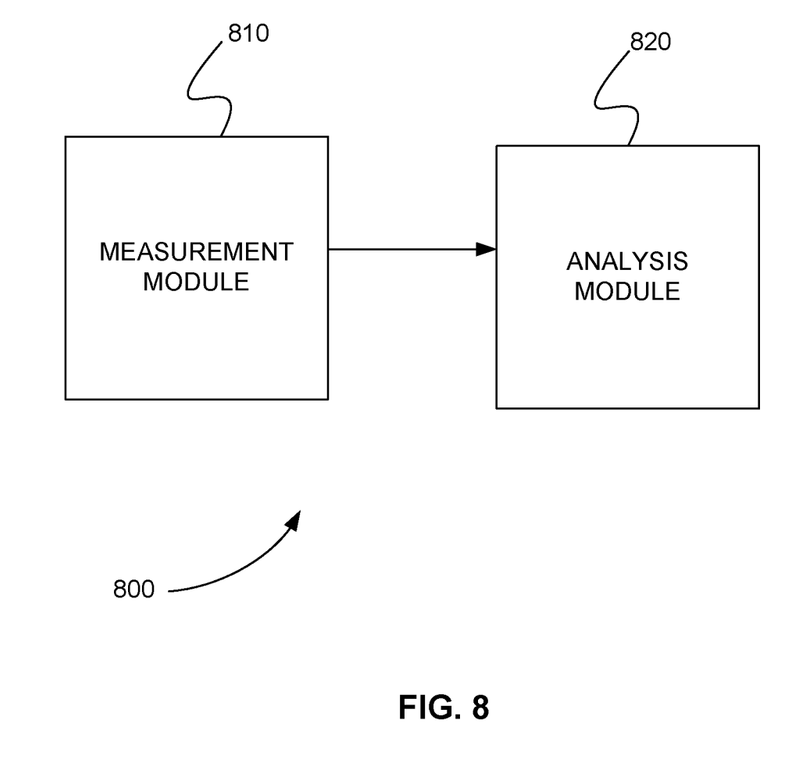
FIG. 8 is a schematic diagram of a system of distinct software modules that performs a method for calculating protein confidence values in proteomic analysis, in accordance with various embodiments.

FIG. 8 is a schematic diagram of a system 800 of distinct software modules that performs a method for calculating protein confidence values in proteomic analysis, in accordance with various embodiments. System 800 includes measurement module 810 and analysis module 820.

Measurement module 810 and analysis module 820 perform a number of steps. Measurement module 810 obtains plurality of spectra from one or more mass spectrometers that perform a plurality of scans of a sample.

Analysis module 820 identifies a plurality of peptides from the plurality of spectra using the analysis module. Analysis module 820 searches a protein database for proteins matching peptides from the plurality of peptides producing a set of proteins and a corresponding set of peptides. Analysis module 820 determines peptide confidence values for the set of peptides. Analysis module 820 calculates a protein confidence value for each protein in the set of proteins based on one or more peptide confidence values of one or more corresponding peptides from the set of peptides. Analysis module 820 selects a protein from the set of proteins with a largest protein confidence value, saves the largest protein confidence value for the protein, removes the protein from the set of proteins, and removes one or more peptides corresponding to the protein from the set of peptides. Analysis module 820 recalculates the protein confidence value for each protein in the set of proteins based on one or more peptide confidence values of one or more corresponding peptides from the set of peptides and an effect of removing the one or more peptides corresponding to the removed protein from the set of peptides.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A method for calculating and recalculating protein confidence values by recalculating peptide confidence values in proteomic analysis in order to distinguish proteins found in a sample from random or false positive results, comprising:
   (a) performing a plurality of scans of a sample that is proteolytically digested into surrogate peptide analytes producing a plurality of spectra using one or more mass spectrometers;
   (b) obtaining the plurality of spectra from the mass spectrometer using a processor;
   (c) identifying a plurality of peptides from the plurality of spectra using the processor;
   (d) searching a protein database for proteins matching peptides from the plurality of peptides producing a set of proteins and a corresponding set of peptides using the processor;

(e) determining peptide confidence values for the set of peptides using the processor, wherein a peptide confidence, Ci, of an $i^{th}$ peptide of the set of peptides is a probability that the ith peptide is identified from the plurality of spectra;

(f) calculating a protein confidence value for each protein in the set of proteins based on one or more peptide confidence values of one or more corresponding peptides from the set of peptides using the processor, wherein a protein confidence value $P_p$ is a probability calculated according to $$P_p=1-\Pi(1-Ci),$$

where $\Pi(1-Ci)$ is the product of one or more peptide confidence values;

(g) selecting a protein from the set of proteins with a largest protein confidence value, saving the largest protein confidence value for the protein, removing the protein from the set of proteins, and removing one or more peptides corresponding to the protein from the set of peptides using the processor;

(h) recalculating the protein confidence value, $P_p$, for each protein in the set of proteins based on one or more peptide posterior probability values of one or more corresponding peptides from the set of peptides according to
$P_p=1-\Pi(1-P(+|B)_i)$ using the processor,
wherein a posterior probability of the $i^{th}$ peptide, $P(+|B)$, of the set of peptides is calculated using $$P(+|B) = \frac{P(B|+) \cdot P(+)}{P(B)}$$

where $P(B|+)$ is the peptide confidence value of the $i^{th}$ peptide, $C_i$, $P(B)$ is the marginal probability of observing the peptide with a given confidence, and $P(+)$ is the prior probability of randomly selecting a true positive and $P(+)$ is calculated from all confidence values of peptides currently in the set of peptides and all confidence values of peptides removed from the set of peptides to account for the effect of removing the one or more peptides corresponding to the removed protein from the set of peptides, and (i) repeating steps (f)-(g) until all proteins are removed from the set of proteins or until a protein confidence value of the selected protein with a largest protein confidence value is below a threshold of interest and identifies proteins found in the sample as the proteins with the saved largest protein confidence values using the processor.

2. The method of claim 1, wherein determining peptide confidence values for the set of peptides comprises using a target-decoy method and the protein database.

3. The method of claim 1, wherein determining peptide confidence values comprises using a heuristic.

4. A computer program product, comprising a tangible computer-readable storage medium whose contents include a program with instructions being executed on a processor so as to perform a method for calculating and recalculating protein confidence values by recalculating peptide confidence values in proteomic analysis in order to distinguish proteins found in a sample from random or false positive results, the method comprising:

(a) providing a system, wherein the system comprises distinct software modules, and wherein the distinct software modules comprise a measurement module and an analysis module;

(b) obtaining a plurality of spectra from one or more mass spectrometers that perform a plurality of scans of a sample that is proteolytically digested into surrogate peptide analytes producing a plurality of spectra using the measurement module;

(c) identifying a plurality of peptides from the plurality of spectra using the analysis module;

(d) searching a protein database for proteins matching peptides from the plurality of peptides producing a set of proteins and a corresponding set of peptides using the analysis module;

(e) determining peptide confidence values for the set of peptides using the analysis module, wherein a peptide confidence, Ci, of an $i^{th}$ peptide of the set of peptides is a probability that the ith peptide is identified from the plurality of spectra;

(f) calculating a protein confidence value for each protein in the set of proteins based on one or more peptide confidence values of one or more corresponding peptides from the set of peptides using the analysis module, wherein a protein confidence value $P_p$ is a probability calculated according to $$P_p=1-\Pi(1-Ci),$$

where $\Pi(1-Ci)$ is the product of one or more peptide confidence values;

(g) selecting a protein from the set of proteins with a largest protein confidence value, saving the largest protein confidence value for the protein, removing the protein from the set of proteins, and removing one or more peptides corresponding to the protein from the set of peptides using the analysis module;

(h) recalculating the protein confidence value, $P_p$, for each protein in the set of proteins based on one or more peptide posterior probability values of one or more corresponding peptides from the set of peptides according to
$P_p=1-\Pi(1-P(+|B)_i)$ using the analysis module,
wherein a posterior probability of the $i^{th}$ peptide, $P(+|B)$, of the set of peptides is calculated using $$P(+|B) = \frac{P(B|+) \cdot P(+)}{P(B)}$$

where $P(B|+)$ is the peptide confidence value of the $i^{th}$ peptide, $C_i$, $P(B)$ is the marginal probability of observing the peptide with a given confidence, and $P(+)$ is the prior probability of randomly selecting a true positive and $P(+)$ is calculated from all confidence values of peptides currently in the set of peptides and all confidence values of peptides removed from the set of peptides to account for the effect of removing the one or more peptides corresponding to the removed protein from the set of peptides, and (i) repeating steps (f)-(g) until all proteins are removed from the set of proteins or until a protein confidence value of the selected protein with a largest protein confidence value is below a threshold of interest and identifies proteins found in the sample as the proteins with the saved largest protein confidence values using the analysis module.

5. The computer program product of claim 4, wherein the analysis module determines peptide confidence values for the set of peptides using a target-decoy method and the protein database.

6. The computer program product of claim 4, wherein the analysis module determines peptide confidence values using a heuristic.

* * * * *